United States Patent [19]
O'Dell et al.

[11] Patent Number: 5,699,747
[45] Date of Patent: Dec. 23, 1997

[54] APPARATUS FOR RESTRAINING VIOLENT DETAINEES

[76] Inventors: Ronald J. O'Dell, 6230 Lakeview Cir., San Ramon, Calif. 94583; Craig J. Zamolo, 1979 Mohawk Dr., Pleasant Hill, Calif. 94523

[21] Appl. No.: 595,598

[22] Filed: Feb. 2, 1996

[51] Int. Cl.⁶ .................................................... A61B 19/00
[52] U.S. Cl. ........................... 128/869; 128/870; 128/876
[58] Field of Search ........................... 128/845, 846, 128/869, 873, 874, 875, 876; 602/19; 5/648, 628, 631

[56] References Cited

U.S. PATENT DOCUMENTS

| | | |
|---|---|---|
| 1,043,648 | 11/1912 | Weaver . |
| 1,047,457 | 6/1912 | Steimer . |
| 2,361,328 | 10/1944 | Springer ................................. 5/628 |
| 2,489,828 | 11/1949 | Springer ................................. 5/625 |
| 2,899,692 | 8/1959 | Finken .................................... 5/628 |
| 3,399,670 | 9/1968 | Veasey . |
| 4,004,583 | 1/1977 | Johnson . |
| 4,027,869 | 6/1977 | Ruiz . |
| 4,173,974 | 11/1979 | Belliveau . |
| 4,204,534 | 5/1980 | Leary . |
| 4,706,957 | 11/1987 | Jackson . |
| 4,725,056 | 2/1988 | Rehrl et al. . |
| 4,742,821 | 5/1988 | Wootan . |
| 4,841,961 | 6/1989 | Burlage et al. . |
| 4,860,560 | 8/1989 | Lindelius . |
| 4,910,818 | 3/1990 | Grahill et al. . |
| 5,016,650 | 5/1991 | Marlar . |
| 5,027,456 | 7/1991 | Wadsworth . |
| 5,031,639 | 7/1991 | Wolfer . |
| 5,190,055 | 3/1993 | O'Connor . |
| 5,193,365 | 3/1993 | Nelson . |
| 5,243,724 | 9/1993 | Barnes . |
| 5,375,277 | 12/1994 | Carr ...................................... 5/628 |

*Primary Examiner*—Michael A. Brown

[57] ABSTRACT

Restraining methods and apparatus for restraining violent detainees, including a rigid binder for binding the upper and lower legs of the detainee, a waist belt, and suspender straps for joining the binder to the waist belt. An erection tether for maintaining the detainee erect by being tautly stretched between an attaching ring at the back of the waist belt and an overhead hook provided for the purpose of maintaining the detainee erect.

17 Claims, 11 Drawing Sheets

APPARATUS FOR RESTRAINING VIOLENT DETAINEES

BACKGROUND OF THE INVENTION

1. Field of the Invention

Our present invention relates to restraining apparatus for use in restraining detainees such as prisoners in police custody or patients in medical facilities, and more particularly to restraining apparatus for restraining violent detainees who, if not suitably restrained, could seriously injure custodial personnel, such as police officers and hospital emergency room personnel, and could also seriously damage public facilities such as the interiors of police patrol cars or ambulances, or the walls, fixtures and furnishings of police station houses, hospitals and the like.

2. Description of the Prior Art

The term "prior art" as used herein or in any statement made by or on behalf of applicants means only that any document or thing referred to as prior art bears, directly or inferentially, a date which is earlier than the effective filing date hereof.

The problem of suitably restraining violent detainees in police and medical facilities is well known and recognized in the prior art.

For example, it is well known in the law enforcement field that substantial injury to an arresting officer or officers and physical damage to public property has resulted when a suspect being taken prisoner has resisted arrest. It has been well known for many years to restrain the hands and arms of a police prisoner by handcuffs or the like which connect the prisoner's hands together in front of or behind his or her body. However, although the legs of the prisoner are powerful weapons, especially when the prisoner is emotionally charged or under the influence of drugs or alcohol, no prior art restraining apparatus or system for violent detainees which has come into general use fully and effectively deals with the problem of protecting personnel and public property from injury or damage produced by kicking by violent detainees. Thus, there are many known cases in which an arresting officer has been kicked violently and seriously injured during the placement of a prisoner in a police patrol car, and also many documented cases wherein a police patrol car, cruiser or squad car, has been badly damaged by a prisoner's feet and legs while the prisoner is being transported to the station house or other detention facility. In certain cases, the entire partition between the police officer and the prisoner has been shattered, although most damage occurs to the doors, side panels and windows of the police patrol car.

In addition to the problem of serious injury to arresting officers and costly damage to public facilities, there is also the problem of the self-infliction by the prisoner of injuries such as bruises, abrasions and even open wounds in order to buttress false claims of police brutality.

In addition to addressing the two abovedescribed problems arising during the initial arrest, transportation and preliminary incarceration of violent detainees, our present invention also addresses the problem of "positional asphyxiation". The now well known term "positional asphyxiation" refers to the fact, or well established belief, that certain prisoners in police custody have suffered asphyxiation with no separate assignable cause during restraint in a prone position, apparently due to post nasal drip or congenital or accidental malformation of the detainee's nasal passages, etc.

These problems result not only in serious injury to police officers and damage to public facilities, in addition to injury or even death of prisoners, but also result in judicial charges of "police brutality", and may thus result in costly litigation and negative publicity.

Other apparatus and systems for restraining violent detainees are found in the prior art, although none of them as fully address all of the problems discussed above, as do the apparatus and systems of the present invention.

U.S. Pat. No. 4,728,553, issued to Jerry Daniels on Mar. 1, 1988, and U.S. Pat. No. 4,784,889, issued to Jerry Daniels on Nov. 15, 1988, both disclose systems for restraining the lower limbs of a prisoner being conveyed in a vehicle, such as a police patrol car, to preclude injury to persons and property by violent kicking action of the prisoner. Both of the patented systems of Daniels include the provision of a laminated fastening strap for encircling the upper legs of the prisoner. Each of the Daniels patents discloses tethering means for tethering said fastening strap to a particular part of a police car in which the prisoner is being transported.

In accordance with the teachings of the Daniels patents, however, the lower legs of the prisoner being transported are unrestrained, leaving the arresting officer and the patrol car in which the prisoner is transported vulnerable to injury and damage brought about by the kicking of the seated prisoner's lower legs.

Further, neither Daniels patent discloses means for constraining the motion of the prisoner's torso, thus leaving the arresting officer subject to injury by violent motion of the prisoner's torso, notwithstanding the fact that the prisoner is handcuffed, with his hands behind his back. Additionally, the freedom of upper torso movement permitted by the systems of the Daniels patents makes it possible for the prisoner to inflict injuries upon himself, such as bruises, abrasions, and even open wounds, which injuries can be calculatedly used to buttress later judicial charges of police brutality.

U.S. Pat. No. 4,852,587, issued to Mark Share on Aug. 1, 1989, discloses a device for subduing and then restraining a violent person comprising a relatively-stiff, bendable shield having opposed major surfaces. One of the major surfaces, designated the back surface, has attached thereto at least two handles, at least one strap, and means for releasably fastening the strap to the back surface.

As shown as FIGS. 2 and 3 of Share, the shield of Share extends substantially from the restrainee's chin to the restrainee's ankles, thus making it difficult if not impossible to bend the restrainee's body to a sitting position suitable for use in transporting the restrainee in a police patrol car.

Further, Share's shield is "a relatively stiff, bendable shield", which is unprovided with integral rigid members which prevent the flexing of the restrainee's legs.

U.S. Pat. No. 4,237,708, issued to Karl W. Bremer, Jr., on Dec. 9, 1980, discloses a prisoner leg restrainer which is attachable to one leg of a prisoner wearing a belt. The leg restrainer of Bremer includes first and second brace elements which are pivotably coupled together by a hinge. Straps are provided to couple the first and second brace elements to the leg of the prisoner. A locking mechanism automatically engages when the upper and lower sections of the leg restrainer are in vertical alignment to prevent pivotal movement of the prisoner's knee.

The leg restrainer of Bremer, being attachable to only one leg of a prisoner, does nothing to protect the arresting officer or officers from being seriously injured by hostile movement of the prisoner's other leg.

In addition, in order to permit a prisoner wearing the leg restrainer of Bremer to assume a seated position, as in a police patrol car, a handle can be manipulated which permits the mutual unlocking of the upper and lower braces, thus "permitting unrestricted aft rotation or pivoting of the leg brace", whereby "the prisoner may flex his knee in a normal manner". Obviously, then, when a prisoner equipped with the device of Bremer is sitting in a police patrol car the device of Bremer does little if anything to protect the arresting officer from injury by the prisoner's legs, or to protect the interior of the patrol car from damage by the prisoner's legs.

It is believed that the documents listed in the Information Disclosure Statement filed herewith contain information which is or might be considered to be material to the examination of this patent application.

SUMMARY OF THE INVENTION

Accordingly, it is an object of our present invention to provide methods, apparatus and systems for safely restraining violent detainees and thus avoiding injury to the detainee and others and avoiding damage to property located near the detainee while the detainee is being transported to or detained at a place of detainment.

Another object of our present invention is to provide apparatus which achieves the above object and which is comprised of but a few structurally simple and rugged elements and thus can be expected to have a long service life, essentially without repair, even though subjected to extremely hard use.

Yet another object of our present invention is to provide apparatus which achieves one or more of the above objects and at the same time is simple in operation, whereby the efficient operation of the apparatus can be taught in a short time at a police academy or like facility and is unlikely to be forgotten under stressful field conditions.

A further object of our present invention is to provide methods, apparatus and systems for safely restraining violent detainees which achieve one or more of the above objects and are of utility not only in police operations but also in medical facilities and the like.

Yet another object of our present invention is to provide methods, apparatus and systems which prevent detainees in police custody from injuring themselves as a hoped for basis for later charges of police brutality.

A yet further object or our present invention is to provide apparatus and systems which achieve one or more of the above objects and at the same time are sufficiently compact and structurally simple to be carried in and readily installed in standard police patrol vehicles.

Another object of our present invention is to provide methods, apparatus and systems which achieve one or more of the above objects and at the same time protect detainees being transported in standard police vehicles from injury resulting from precipitate motions unavoidably executed by the drivers of such vehicles.

Yet another object of our present invention is to provide methods, apparatus and systems which achieve one or more of the above objects and at the same time protect detainees restrained thereby from positional asphyxiation.

Other objects of our present invention will in part be obvious and will in part appear hereinafter.

Our present invention, accordingly, comprises the several steps and the relation of one or more of such steps respect to each of the others, and the apparatus and systems embodying features of construction, combinations of elements, and arrangements of parts which are adapted to effect such steps, all as exemplified in the following disclosure, and the scope of our present invention will be indicated in the claims appended hereto.

In accordance with a principal feature of our present invention methods, apparatus and systems for safely restraining violent detainees are provided which include leg binder means for binding together the legs (both upper and lower) of the detainee.

In accordance with another principal feature of our present invention said leg binding means is comprised of a panel of heavy-duty flexuous sheet material, such as leather, canvas or certain plastic materials, mesh or netting, or perforate sheet material.

In accordance with yet another principal feature of our present invention, the greatest longitudinal dimension of said binder is preferably equal to or slightly less than the distance between the ankles and the upper thighs of a short human being whose legs are straight, and the greatest transverse dimension of said binder is such that the binder can be tightly bound around the substantially unflexed (straight) legs of a heavy or very muscular detainee with an overlap of about one-quarter of the maximum peripheral dimension of the detainee's upper legs.

In accordance with a further principal feature of our present invention, said binder is provided with binder closure means such as a plurality of heavy binding straps, and associated fasteners, whereby the binder may be bound around the legs (upper and lower) of the detainee.

In accordance with a further principal feature of our present invention, a plurality of rigid members, sometimes called "steels" are incorporated into said binder for preventing the detainee from bending his knees, and preventing the detainee from making hostile use of his heavy thigh muscles.

In accordance with another principal feature of our present invention, the restraining apparatus of certain embodiments of the invention includes a cincture such as a waist belt which may be fastened around the detainee's waist, and suspender straps which are affixed to the waist belt and the binder, thereby preventing the detainee from doffing the binder.

In accordance with another principal feature of our present invention, wrist positioning means such as wrist cuffs each of which is comprised of straps joinable by pileate fastening means are affixed to said cincture or waist belt, whereby the wrists of the detainee may be affixed to said waist belt at such positions that when the detainee is seated his doubled fists will be located in respective positions directly above his thighs.

In accordance with yet another principal feature of our present invention a ring is secured to said waist belt, behind the detainee and near his spine, which ring is adapted to receive the linking member of a pair of handcuffs, making it possible to apply the apparatus of our invention to the detainee without removing the handcuffs which were previously applied to the wrists of the detainee.

In accordance with yet another principal feature of our present invention, a short, taut erection tether may be affixed to said ring, and the opposite end of said erection tether affixed to a tethering ring which is fixedly and securely mounted in a police patrol car in which the detainee is being transported, thus preventing the detainee from shifting his torso from side to side in the patrol car and protecting the detainee from injury in the event that the driver of the patrol car finds it necessary to precipitously maneuver the patrol car in order to avoid an accident, or the like.

In accordance with a further principal feature of our present invention, a detainee restrained in restraining apparatus of our invention, e.g., in the booking room of a police station, and seated with his back to a wall, may be protected from positional asphyxiation by an erection tether extending from the handcuff ring at the back of the waist belt of the apparatus to a wall-mounted hook located directly above the detainee's head.

For a fuller understanding of the nature and objects of our present invention, reference should be had to the following detailed description, taken in connection with the accompanying drawings.

BRIEF DESCRIPTION OF THE DRAWINGS

FIG. 1A is a partial cross-sectional view of the binder of the first preferred embodiment of the present invention as seen in FIG. 1, taken on any of the perpendicular planes 1A—1A of FIG. 1;

DESCRIPTION OF THE PREFERRED EMBODIMENTS

Referring now to FIGS. 1, 1A, 2, 3, 4 and 5, there is shown a restraining device 10 of our present invention for restraining violent detainees in accordance with the principles of our invention.

It is to be understood that restraining device 10 is shown in its entirety only in FIG. 5, the preceding figures showing the principle parts of restraining device 10 which are sometimes hereinafter designated by the terms "binder", "waist belt", "wrist cuffs", and "suspender straps".

Figure 1:
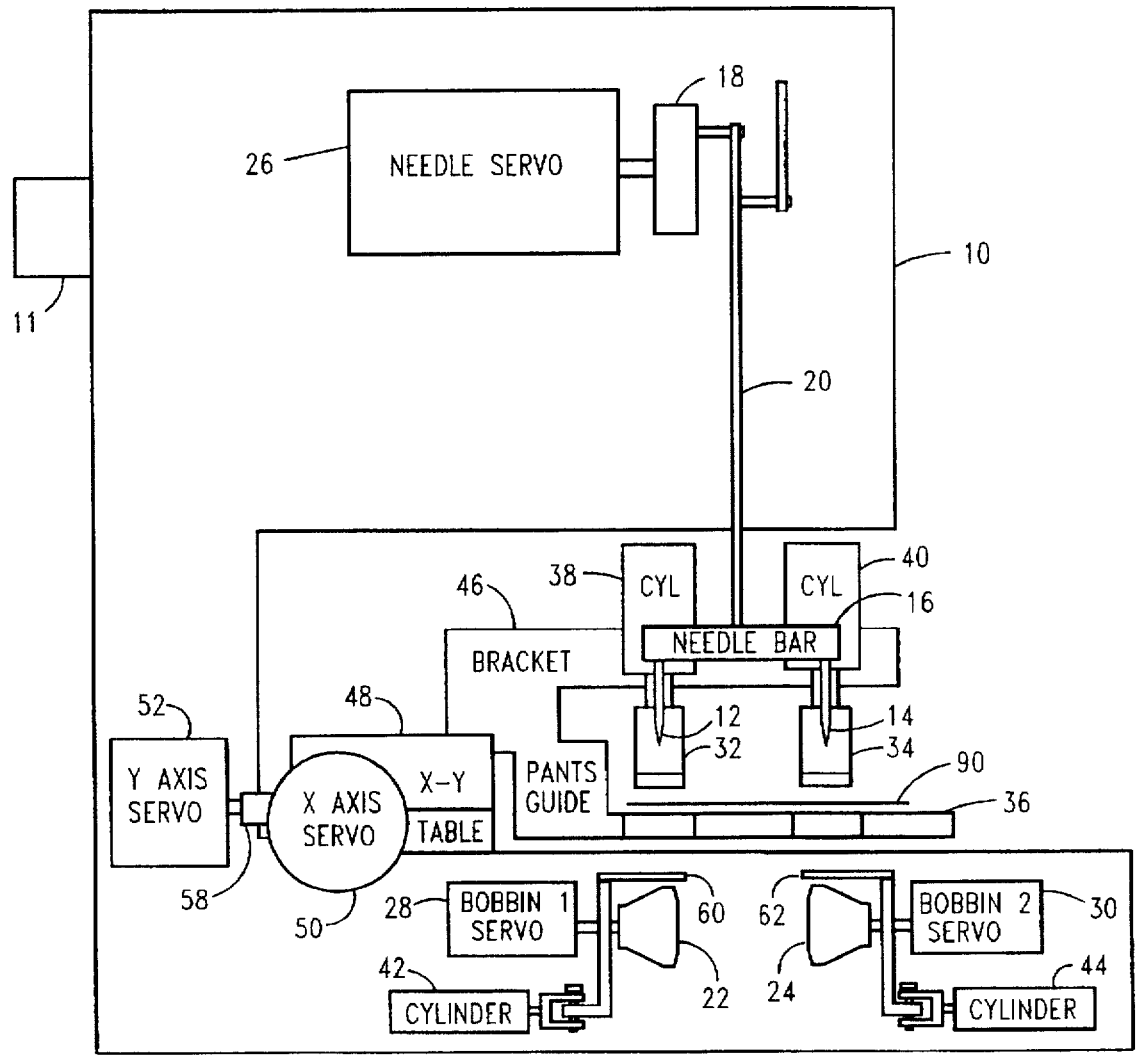
FIG. 1 is a plan view of the inside face of the binder of the first preferred embodiment of the present invention as disposed on a horizontal surface.
Figure 2:
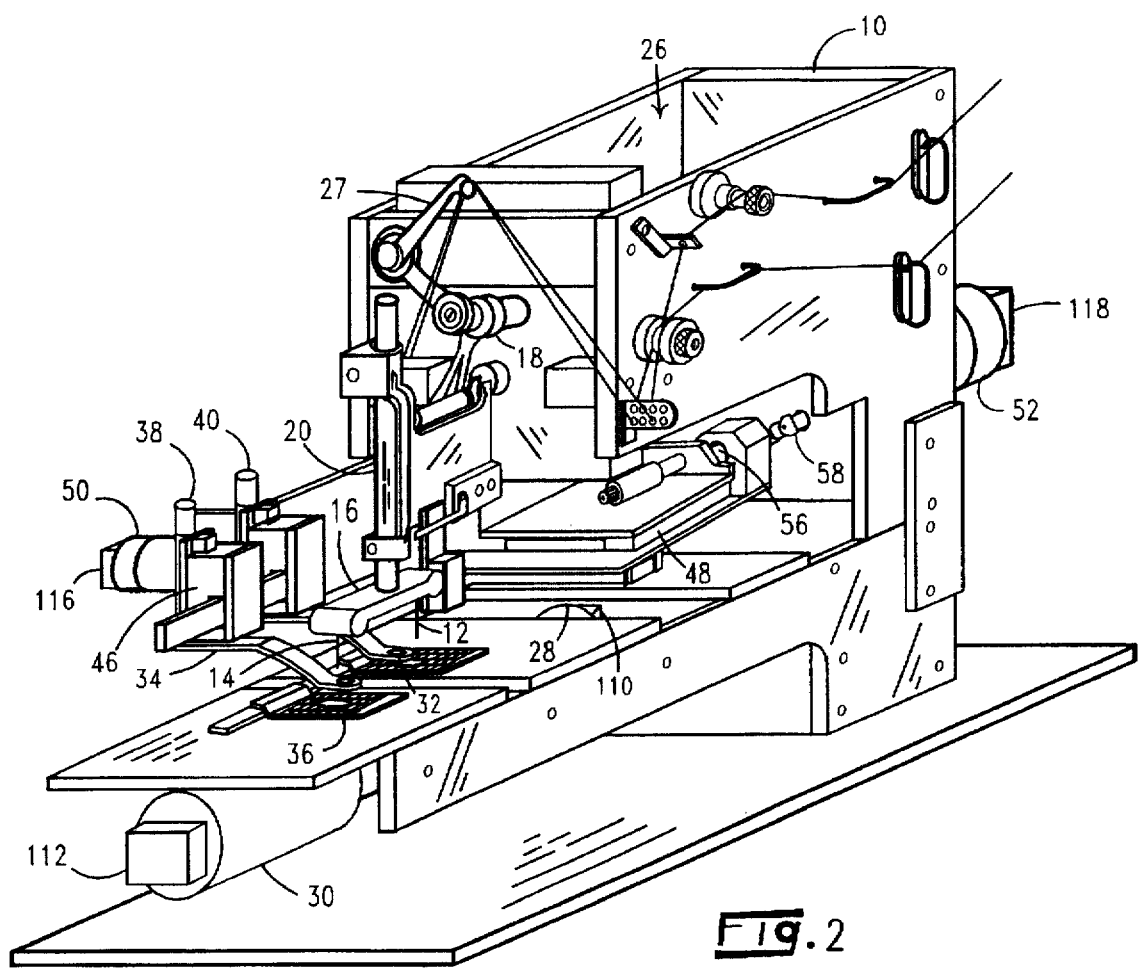
FIG. 2 is a plan view of the outer face of the binder of the first preferred embodiment of the present invention as disposed on a horizontal surface.

Referring now to FIGS. 1 and 2, it will be seen that restraining device 10 is comprised of a sheet or panel 12 of heavy-duty, flexuous sheet material, such as leather, canvas or certain plastic materials, or certain foraminous materials.

Sheet or panel 12 will sometimes hereinafter be called the "binder body".

As best seen in FIG. 1, three elongated pockets 14 are sewn to binder body 12, and extend substantially from upper edge 16 to lower edge 18 of binder body 12, between side edges 15 and 17 thereof.

As best seen by comparison of FIG. 1 and FIG. 1A, each of the pockets 14 contains a rigid steel tube 20, sometimes called a "steel" or leg flexure preventing means herein. Each steel tube 20 is captive in its associated pocket 14.

Other embodiments of our invention max comprise more or less steels than three, or may comprise but one steel.

In some embodiments the steel or steels may be angulated, rather than rectilinear.

In some embodiments of the present invention a solid, rigid steel rod may be substituted for each of the tubular members 20 of the first preferred embodiment.

Referring now to FIG. 2, it will be seen that three binding straps 22 are sewn to the outer surface of binder body 12.

As best seen in FIG. 2, the inner portion 22.1 of each binding strap 22 is sewn to binder body 12.

Further, as also seen in FIG. 2, an elongated free end 22.2 of each binding strap 22 is not secured to binder body 12.

The free end 22.2 of each binding strap 22 may also sometimes be called the "outer end" of that binding strap herein.

As also seen in FIG. 2, the inner end 23 of each binding strap 22 is provided with a square ring 24 which is capable of receiving the free end 22.2 of the same binding strap 22. One leg of each ring 24 is captive in a sewn loop formed from the inner end 23 of its associated binding strap 22.

Preferably, each square ring 24 is provided, in the well known manner, with a rotatable sleeve 26, whereby the "cinching up" of each binding strap 22 about binder body 12 and the legs of the detainee is rendered easier.

As yet further seen in FIG. 2, the free end 22.2 of each binding strap 22 is provided with two attached patches 28, 30 of pileate fastening material, such as Velcro. Each pair of patches 28, 30 affixed (as by sewing) to one binding strap 22 are so mutually juxtaposed that when an outer part of free end 22.2 is passed through associated ring 24 the outer part of free end 22.2 (bearing hook-type pileate fastening material 28) can be fastened to its associated (loop-type) patch 30 of pileate fastening material by pressing these patches 28, 30 together, and thus this free end 22.2 can be affixed to its associated ring 24.

As also seen in FIG. 2, a pair of adjustable strap anchors 32 are respectively affixed to binder body 12, as by means of loops 33 of belting material, each of which embraces a leg of its associated strap anchor 32 and is sewn to binder body 12.

As further seen in FIG. 2, each one of a pair of suspender straps 40 is engaged with an associated one of said strap anchors 32, and thus is adjustably secured to binder body 12.

As will now be understood by those having ordinary skill in the art, informed by the present disclosure, the length of each suspender strap 40 extending outwardly from its associated strap anchor 32 is adjustable by repositioning that suspender strap in its associated strap anchor 32.

Figure 3:
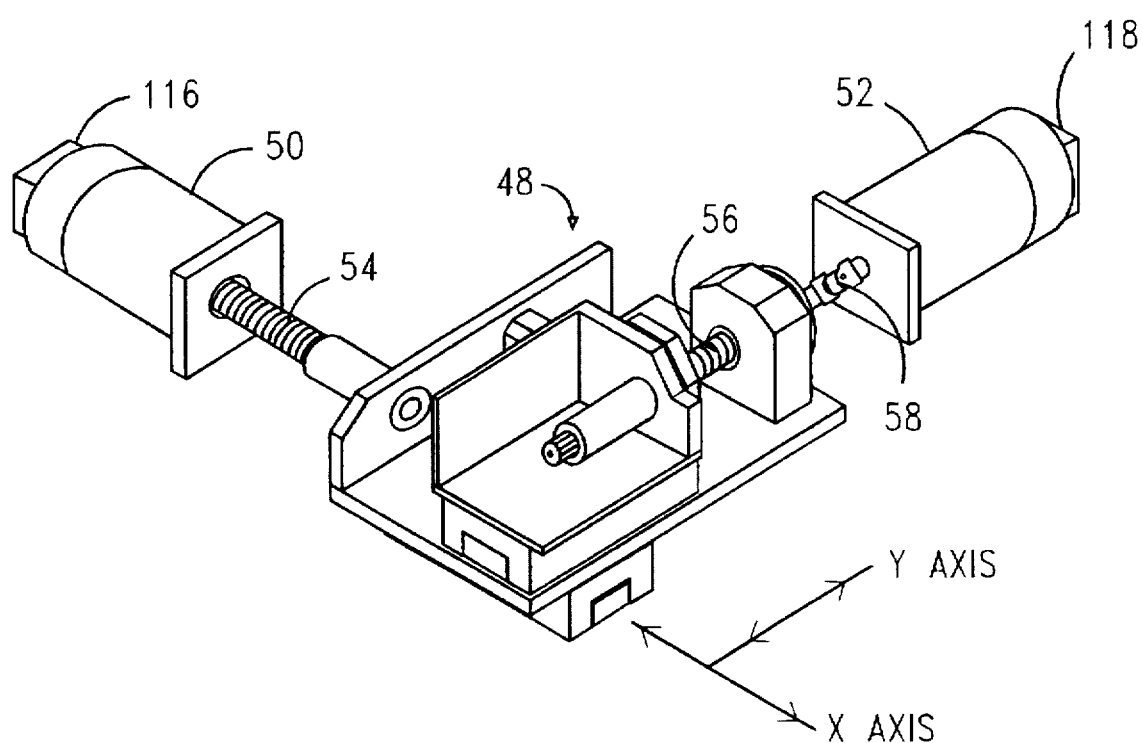
FIG. 3 is a plan view of the inner face of the waist belt assembly of the first preferred embodiment of the present invention, including the waist belt and the wrist cuffs, and a partial showing of the suspender straps, as disposed on a horizontal surface.
Figure 4:
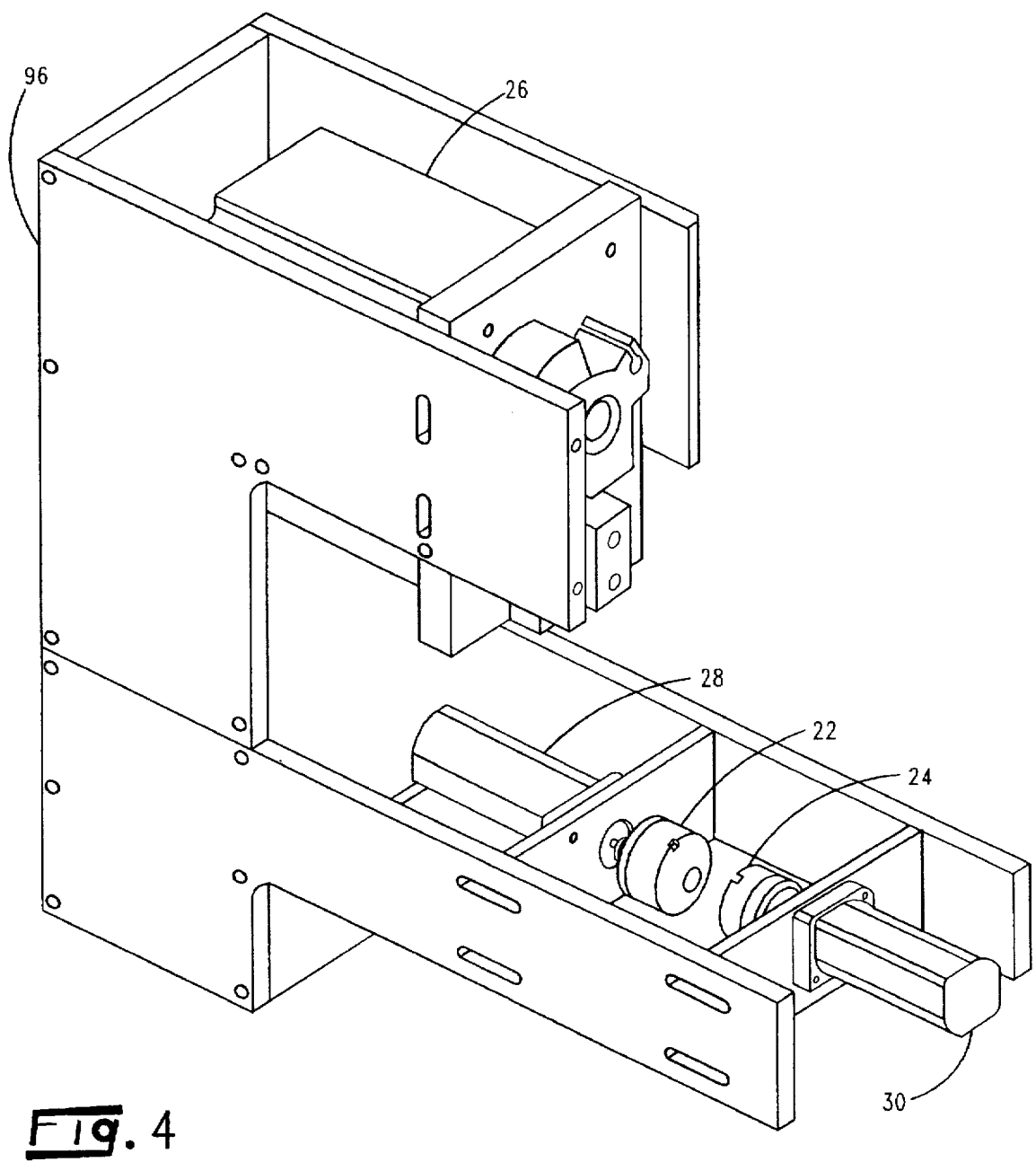
FIG. 4 is a partial plan view of the outer face of the waist belt assembly of the first preferred embodiment of the present invention as disposed on a horizontal surface.

Referring now to FIGS. 3 and 4, it will be seen that the end of each suspender strap 40 remote from binder body 12 is sewn to a cincture or waist belt 42.

In accordance with a principal feature of our invention, waist belt 42, in use, is fastened about the waist of the detainee; and thus, through the intermediation of suspender straps 40, cincture or waist belt 42 prevents the detainee from thrusting binder body 12 away from his waist and over his feet, i.e., from doffing the binder.

Binder body 12 and its associated parts described hereinabove, but excepting suspender straps 40, are sometimes collectively called "the binder" herein. The "binder" is designated herein by the reference numeral 44.

As seen in FIG. 3, cincture or waist belt 42 is comprised of an elongated piece of belting material 46, e.g., woven belting.

As also seen in FIG. 3, one end of belting material 46 is formed into a sewn loop 48, and one side of a square ring 50 is captive within loop 48.

It is to be understood that ring 50 is similar to the rings 24 shown in FIG. 2 and described hereinabove, and that ring 50 is provided with a rotatable sleeve 52 similar in structure and function to the rotatable sleeves 26 of rings 24.

As seen in FIG. 4, a panel of hook-type pileate fastening material 54 is affixed to belting material 46, and a panel of loop-type pileate fastening material 56 is also affixed to belting material 46.

Thus, as will be understood by those having ordinary skill in the art, informed by the present disclosure, waist belt 42 may be fastened about the waist of the detainee by passing the free end 42.1 of waist belt 42 underneath and through ring 50, cinching waist belt 42 about the waist of the detainee, and then pressing the confronting faces of pileate fastening material panels 54, 56 together in the well known manner.

As also seen in FIG. 4, two wrist cuffs 60 are secured to waist belt 42 by stitching. Each wrist cuff 60 is comprised of a wrist strap 61 and a square ring 64, which is joined to waist belt 42 by a joining strap 62. Each joining strap 62 is affixed at its opposite ends, by stitching, to waist belt 42 and thus forms a loop in which a leg of its associated ring 64 is captive.

As seen in FIG. 3, each wrist cuff 60 is further comprised of two patches of pileate fastening material 66, 68. The inner end 61' of each wrist strap 61 is sewn to waist belt 42, as seen in FIG. 4.

Thus, it will be understood by those having ordinary skill in the art, informed by the present disclosure, that each wrist cuff 60 can be secured about one of the detainee's wrists in substantially the same manner in which waist belt 42 is secured about the detainee's waist.

As will be evident to those having ordinary skill in the art, patches 66 are fabricated from pileate fastening material of the hook type, and patches 68 are fabricated from pileate fastening material of the loop type. Thus, it will be understood that any patch of pileate fastening material shown in the drawings and shaded in the same manner as patches 66 in FIG. 3 is a patch of hook-type fastening material, and that any patch of pileate fastening material shown in the drawings which is shaded in the manner of pileate fastening material patches 68 of FIG. 3 is to be understood to be a patch of loop-type pileate fastening material.

A carrying handle 70 (FIG. 2) is affixed to binder body 12 to be used in transporting any detainee restrained in restraining device 10.

Referring again to FIGS. 3 and 4, it will be seen that a square ring 74 is mounted on waist belt 42, closely adjacent the above-described square ring 50.

As best seen in FIG. 4, a short piece of belting material 76 is bent upon itself to form a loop 77 and is then sewn to waist belt 42 with a leg of square ring 74 captive therein.

As also seen in FIG. 4, one leg of square ring 74 is captive within loop 77, and thus square ring 74 is pivotable about the axis of loop 77.

As further seen in FIG. 4, square ring 74 is generally C-shaped, and thus has two open ends 78, 78', both of which are threaded.

As also seen in FIG. 4, a nut 80 is threadedly engaged with the threads of open end 78', and nut 80 can thus be rotated about its axis to either (1) open the gap between itself and open end 78 or (2) move toward open end 78 and engage with the threads thereof.

Thus, it will be seen that by manipulation of nut 80 square ring 74 can be opened or completely closed.

It is to be understood that the maximum gap in ring 74 produced by the manipulation of nut 80 is sufficiently large to receive the linking member of a pair of handcuffs; and that thus, by manipulating nut 80 after locating the linking member of a pair of handcuffs in ring 74, that pair of handcuffs can be affixed to waist belt 42.

The term "waist belt assembly" as used herein denotes waist belt 42 (FIGS. 3 adn 4) and wrist cuffs 60, but does not include within its denotation the associated suspender straps 40. The waist belt assembly is sometimes designated herein by the reference numeral 45 (FIGS. 3 and 4).

Figure 5:
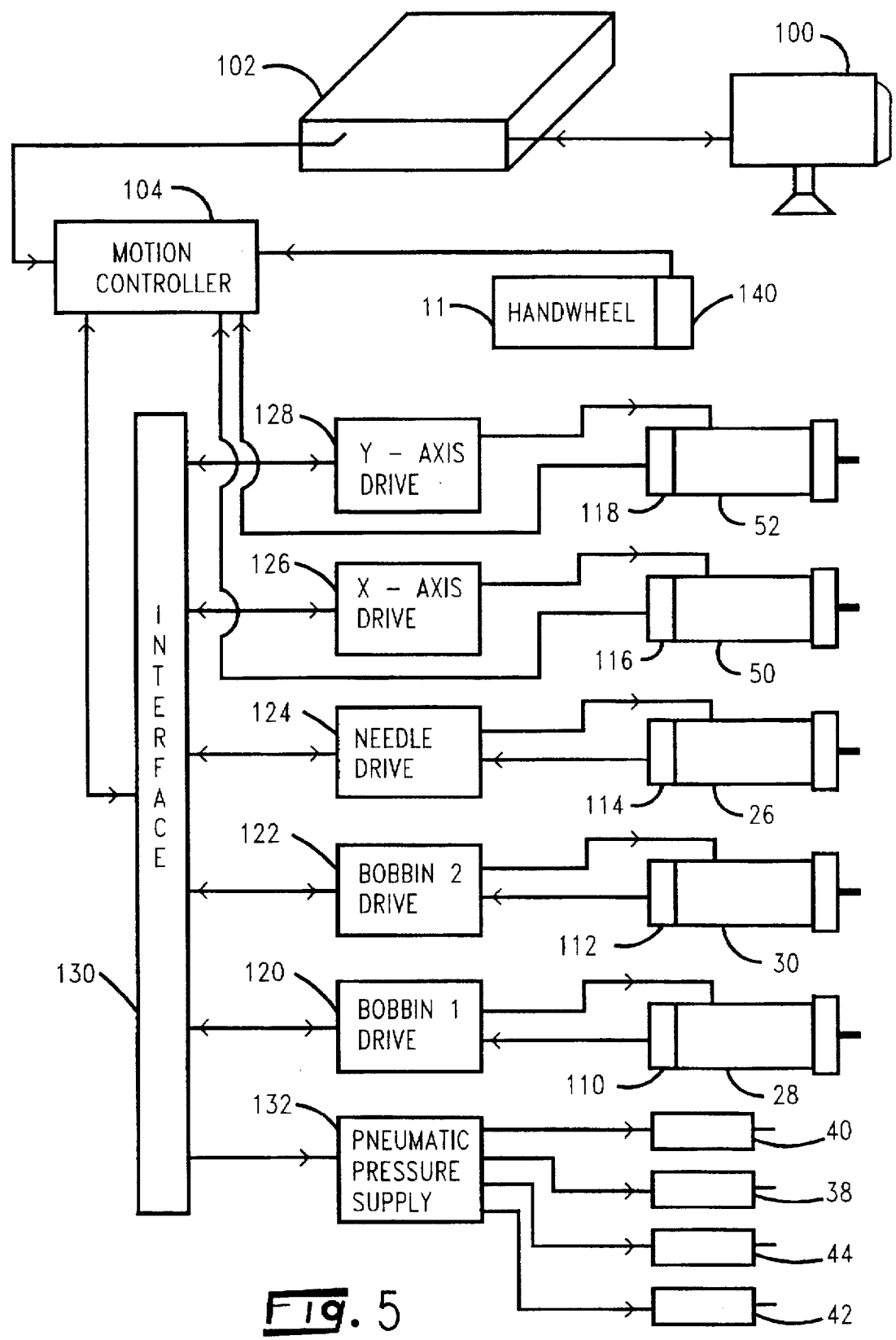
FIG. 5 is a plan view of the inner face of the restraining device of the first preferred embodiment of the present invention as disposed on a horizontal surface.
Figure 6A:
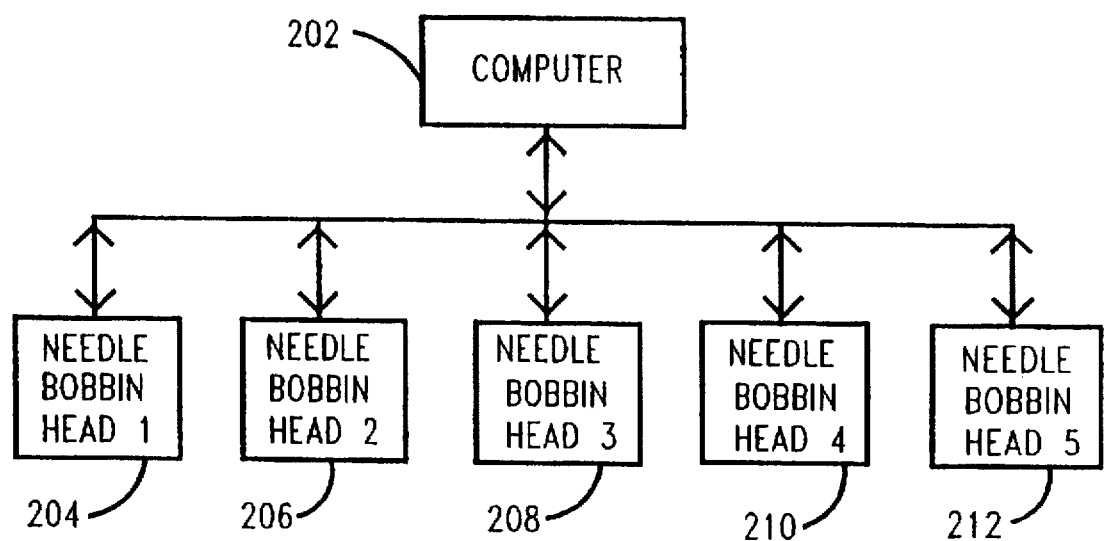
FIG. 6 is a perspective view of a detainee lying prone and restrained by a restraining device of the first preferred embodiment of our present invention.
Figure 6B:
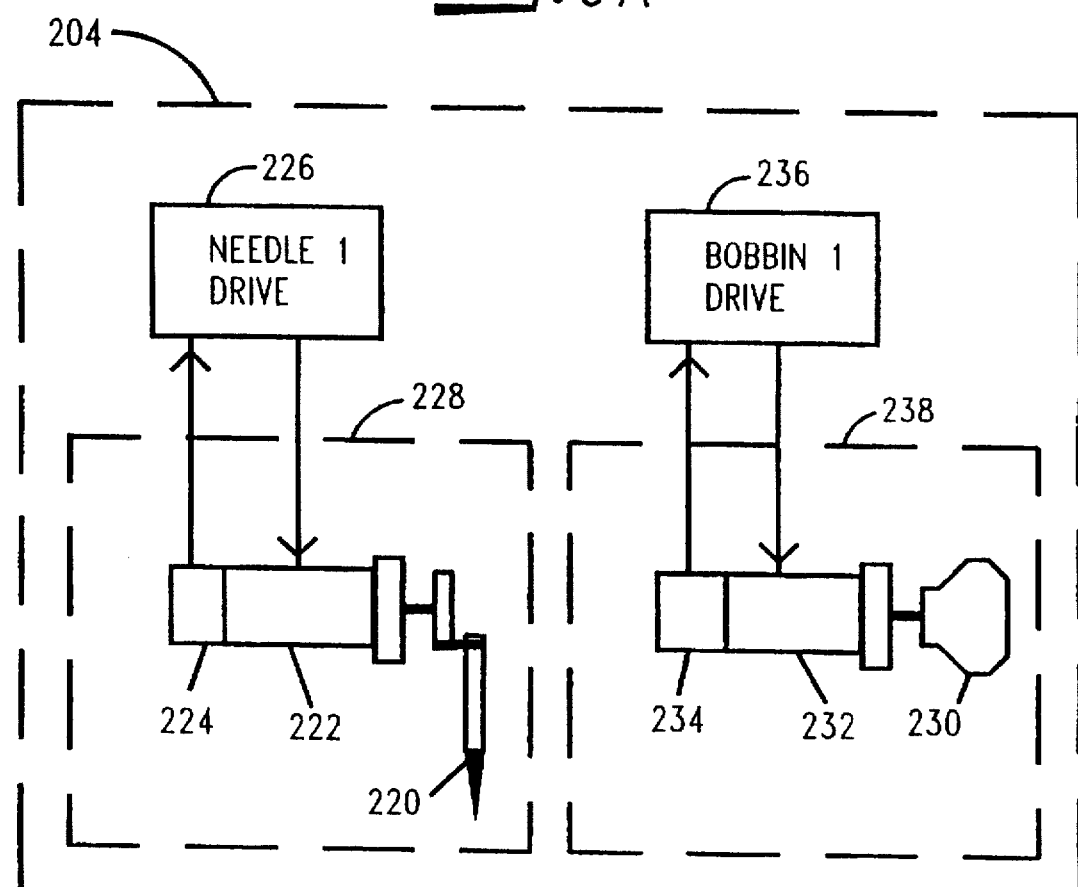
Figure 6C:
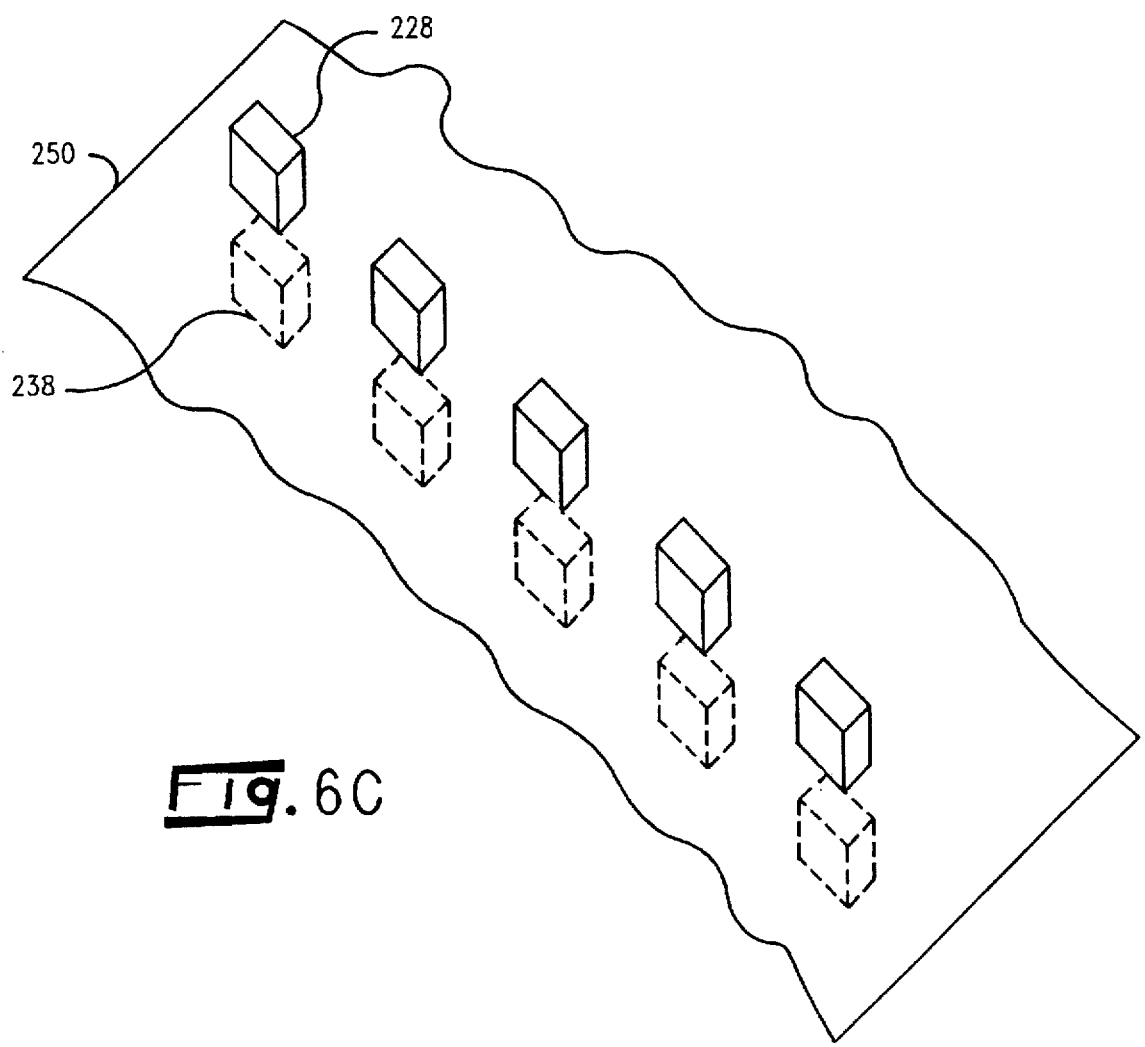

Referring now to FIG. 5, there is shown a complete restraining device 10 of the preferred embodiment of our present invention. The complete restraining device 10 consists of binder 44, waist belt assembly 45, and two suspender straps 40.

As taught hereinabove in connection with FIGS. 1, 2, 3, and 4, suspender straps 40 are sewn to waist belt 42 and adjustably affixed to binder 44 by means of adjustable strap anchors 32 (FIG. 2), whereby the distance between binder 44 and waist belt assembly 45 can be adjusted to accommodate the respective body dimensions of different detainees.

Figure 6:
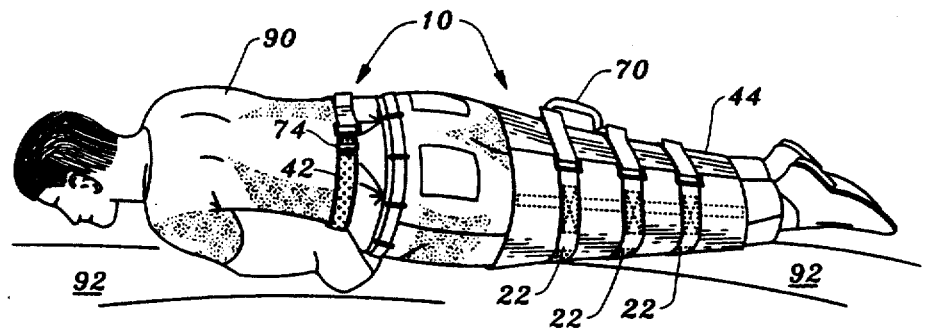
Figure 7:
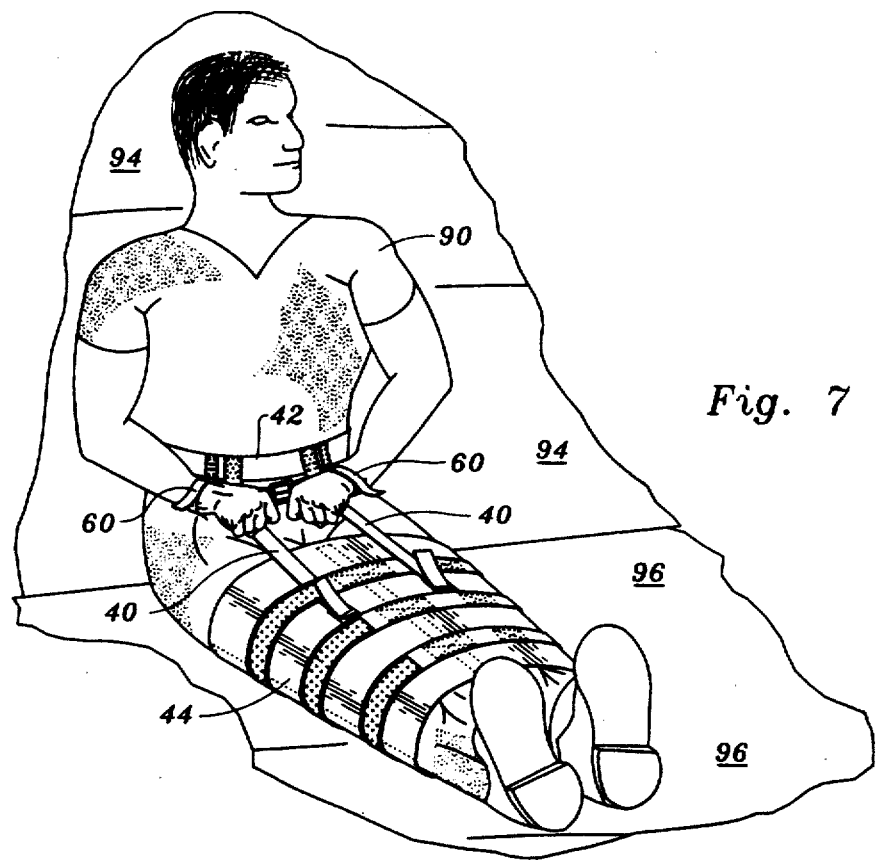
Figures 8, 9:
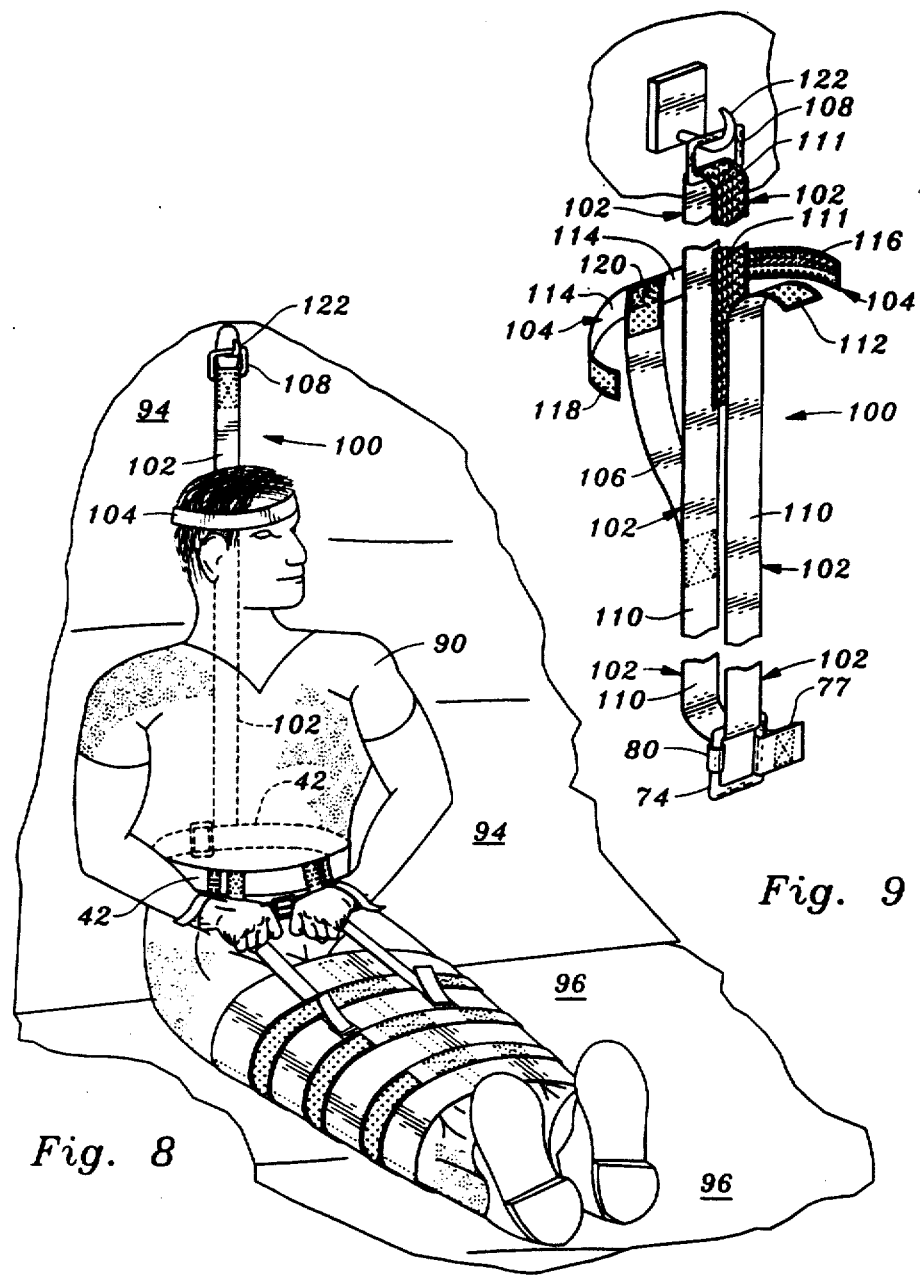

Referring now to FIG. 6 there is shown a particular detainee 90 as he appears immediately after he has been bound in restraining device 10.

As seen in FIG. 6, detainee 90 lies prone on floor 92 immediately after he has been bound in restraining device 10.

As also seen in FIG. 6, handcuff ring 74 (FIGS. 3 and 4) is located at the rear of waist belt 42 immediately adjacent to the spine of detainee 90 whenever detainee 90 is bound in restraining device 10.

Restraining device 10 is preferably applied to detainee 90 by first spreading restraining device 10 on a floor or other horizontal surface with its inner face, i.e., the face thereof which will confront the body of the detainee, upward, as shown in FIG. 5. Detainee 90, who is immobilized, e.g., by a well known TASERTRON device, is then placed on top of restraining device 10 with his upper and lower legs disposed over binder 44. Binder 44 is then wrapped around the upper and lower legs of detainee 90 and is bound around the detainee's legs by means of binding straps 22.

It is to be understood that while the detainee's hands are located beneath his body in FIG. 6, the wrist cuffs 60 of restraining device 10 have not been applied to the detainee's wrists in FIG. 6. Rather, detainee 90 is first brought into a sitting position (FIG. 7), preferably with his back against a vertical support, and with his bound legs disposed upon a horizontal supporting surface. Wrist cuffs 60 are then applied to the wrists of detainee 90.

Figure 7:
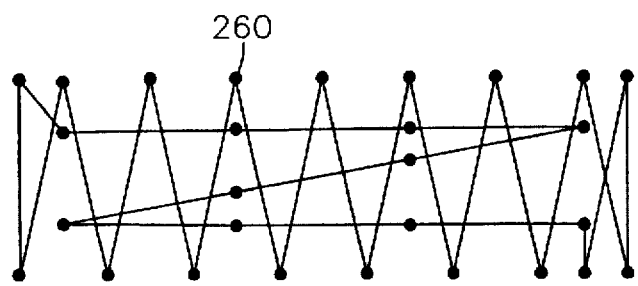
FIG. 7 is a perspective view of a detainee restrained in a restraining device of the first preferred embodiment of the present invention, seated on the floor of a room and leaning against a wall of that room.

Detainee 90 is then transported to a holding facility and placed against a wall 94 with his legs disposed upon the associated floor 96 as seen in FIG. 7.

It is to be understood that while the wrists of detainee 90 are confined in wrist cuffs 60 in FIG. 7 it may be preferred, within the scope of our invention, to fasten detainee's wrists behind his back by applying a pair of handcuffs to his wrists, and then, after he has been bound in restraining device 10, clamping the chain or other linking member of said handcuffs in handcuff ring 74 so that the detainee's hands are fastened behind his back.

Figure 8:
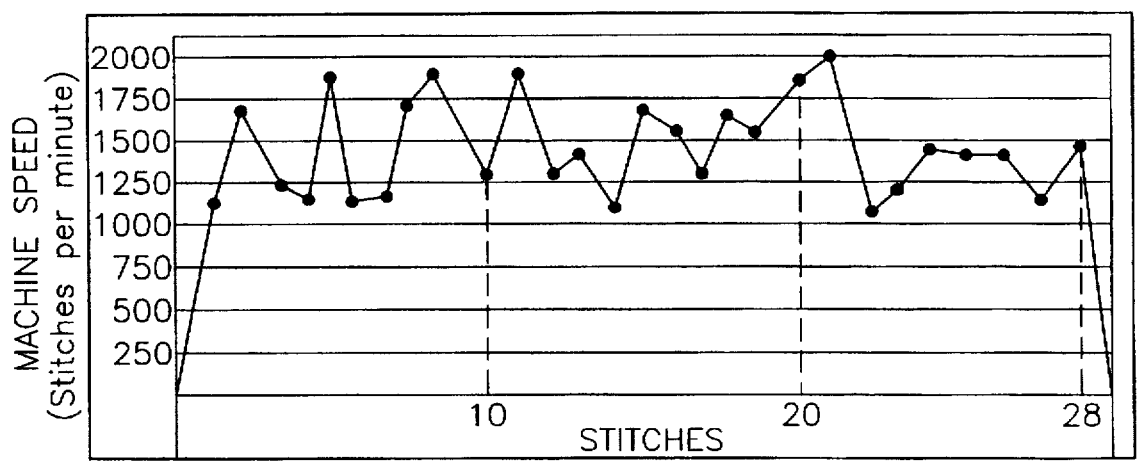
FIG. 8 is a perspective view corresponding to the perspective view of FIG. 7 and additionally showing an erection tether system of our present invention.
Figure 9:
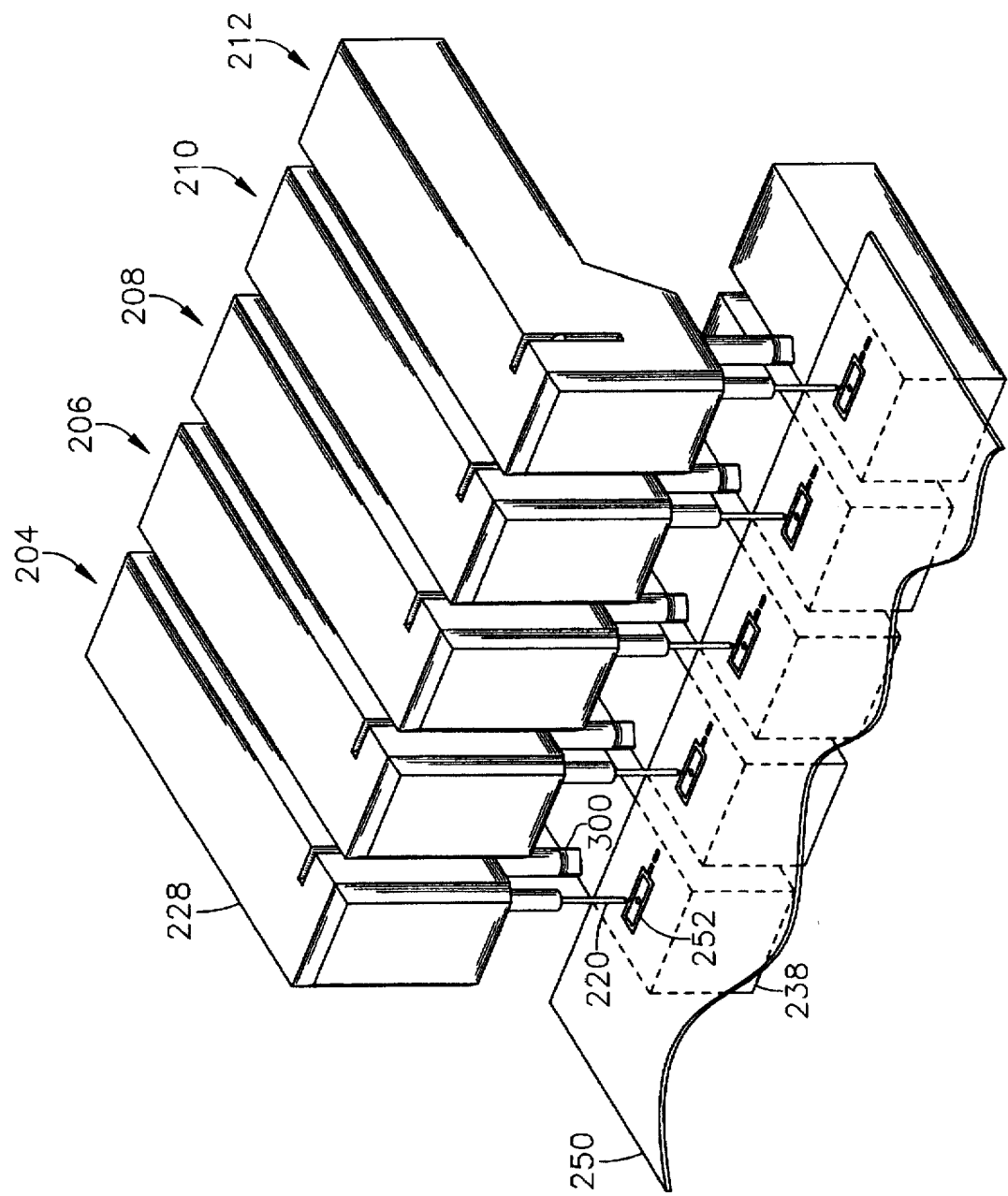
FIG. 9 is a perspective view of said erection tether system of the first preferred embodiment of the present invention.
Figure 10:
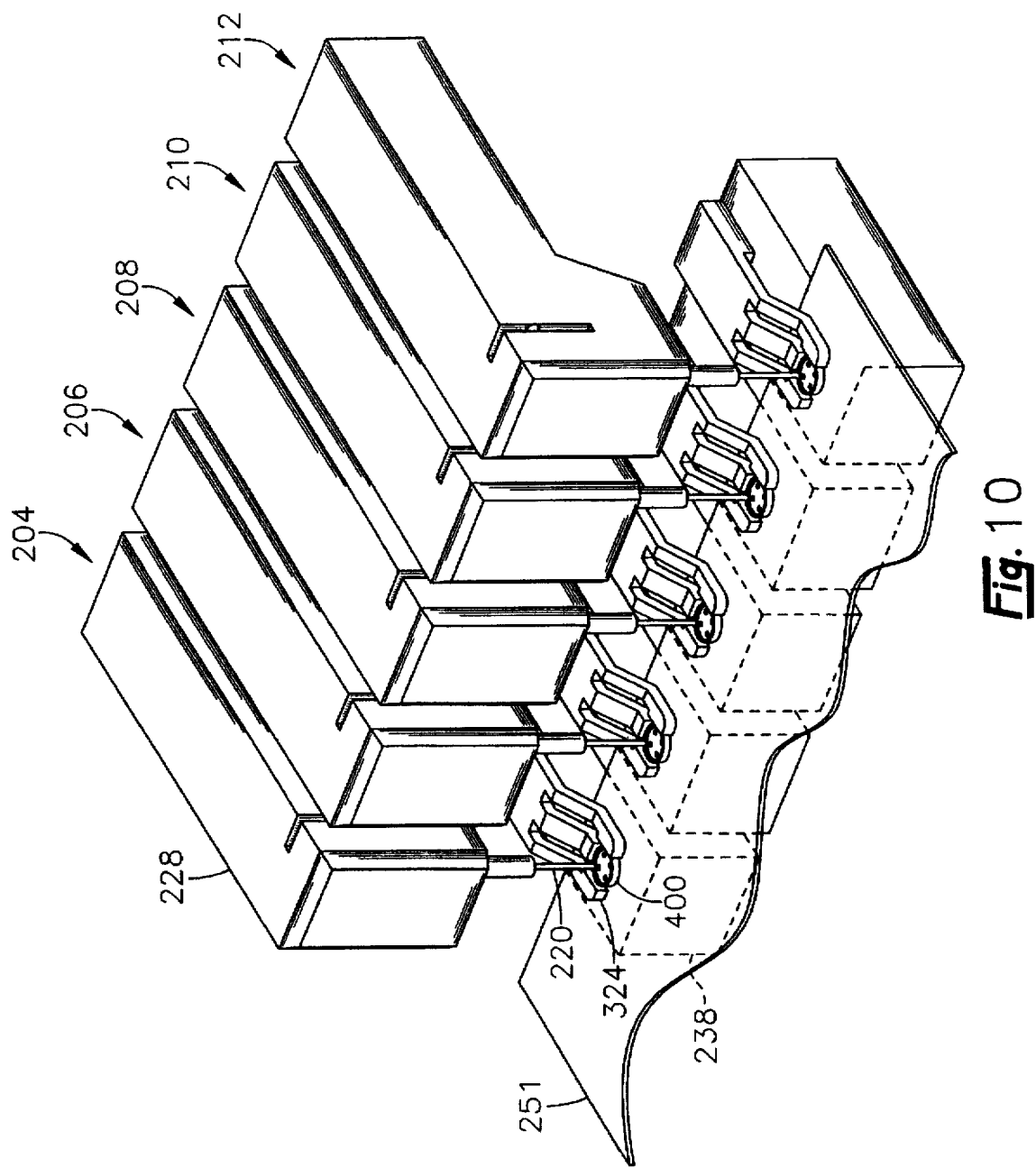
Figure 11:
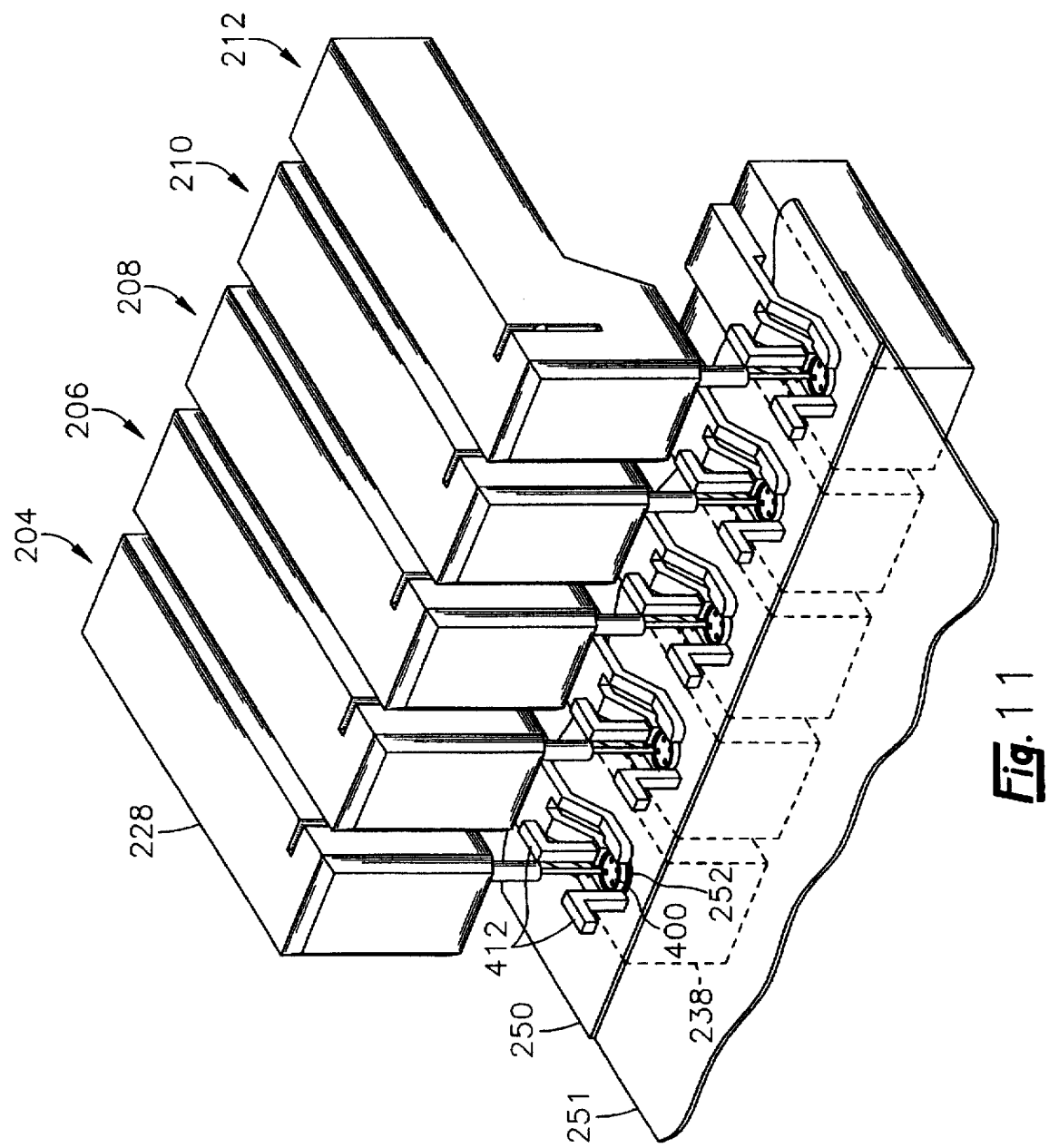
Figure 5:
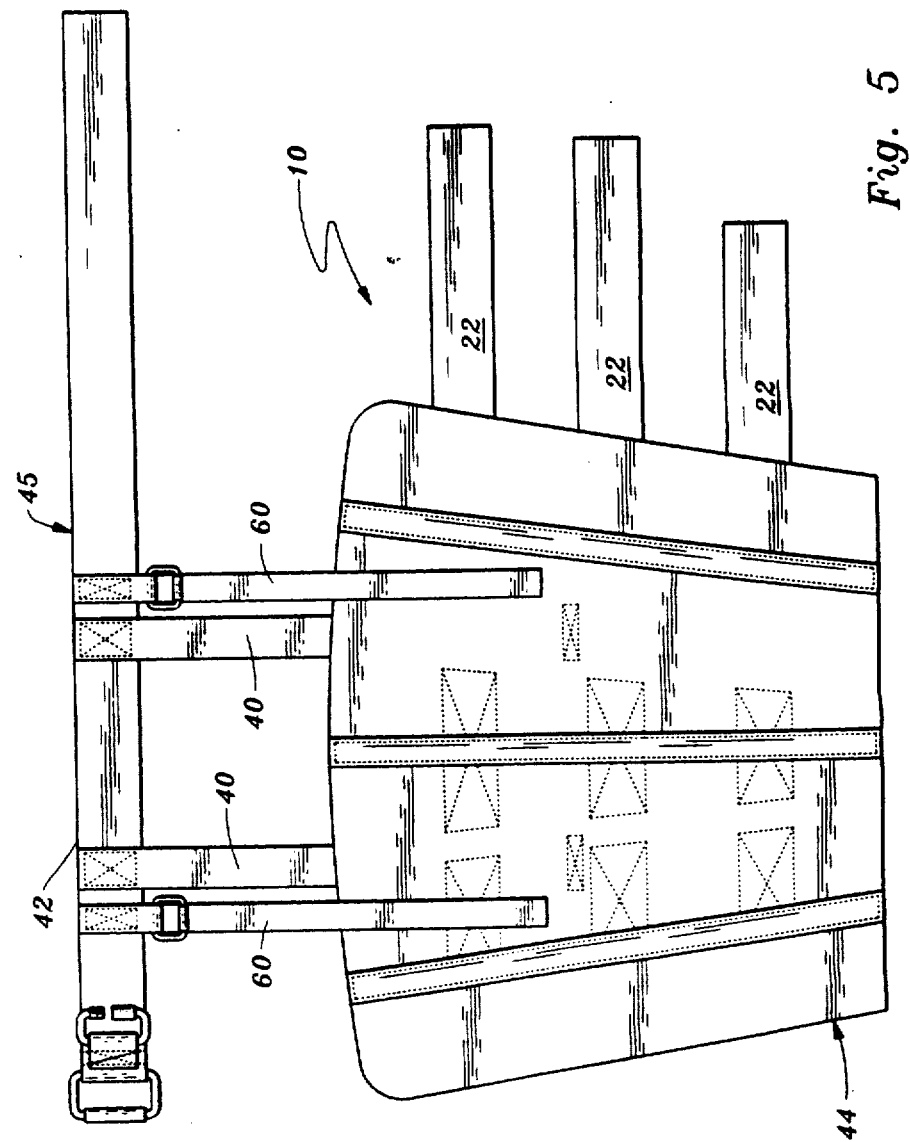

Referring now to FIGS. 8 and 9, there is shown an erection tether 100 which is a principal feature of our present invention.

As is well known in the literature of penology, detainees who were bound in a horizontal position have been known to die of what is currently called "positional asphyxiation". Further, detainees who are free to thrash from side to side have been known to intentionally injure themselves, sometimes in an attempt to provide a basis for later false charges of police brutality.

The function of erection tether 100 of our present invention, then, is to reduce or prevent the occurrence of positional asphyxiation and the self-infliction of injuries by detainees.

It is to be understood that FIG. 8 differs from FIG. 7 only in that the torso of detainee 90 is kept erect by means of erection tether 100 of our present invention, which is not shown in FIG. 7.

It is further to be understood that while erection tether 100 is a part of our present invention its use in connection with restraining device 10 of our invention is not necessarily required. Thus, for example, personnel in charge of violent detainees may decide to use only restraining device 10 in connection with a particular detainee or detainees, and may decide to use both restraining device 10 and erection tether 100 in connection with another detainee or detainees.

Referring now to FIG. 9, it will be seen that erection tether 100 of our invention is comprised of a loop 102 of belting material, a headband 104, a headband tether 106 and a square ring 108.

As also seen in FIG. 9, loop 102 is comprised of a segment of belting material 110 to which are adhered, as by sewing, a length of hook-type pileate fastening material 111, e.g., Velcro, and a length of loop-type pileate fastening material 112, e.g., Velcro. Loop 102 is passed through square ring 108 and also through square ring 74 (which is secured to the back of waist belt 42 as seen in FIGS. 3, 4 and 6) by means of a short loop of belting material 77 (FIG. 4).

As will be evident to those having ordinary skill in the art, informed by the present disclosure, the length and tautness of loop 102 may be altered by separating pileate material fasteners 111, 112 (FIG. 9); repositioning these segments with respect to each other until loop 102 is taut, and then pressing pileate material segments 111, 112 together throughout their mutually confronting face areas.

Also a part of erection tether 100 is a headband 104. Headband 104 is principally comprised of a segment of belting material 114. A segment of hook-type pileate fastening material 116 is affixed to one end of belting material 114, on a first side thereof, and a segment of loop-type pileate fastening material 118 is affixed to the other end of belting material 114 on the opposite side thereof from pileate fastening material segment 116. By this means headband 104 can be tightly secured around the head of detainee 90. For convenience, headband tether 106 is provided. Headband tether 106 is sewn at its lower end to loop 102, and at its upper end to headband 104. A patch 120 of loop-type pileate fastening material is affixed to headband 104 in such a position that it can be made to confront a selected part of hook-type pileate fastening material segment 111, and thus headband 104 can be prevented from moving along loop 102.

Referring now to FIG. 8, and comparing it with FIG. 9, it will be evident to those having ordinary skill in the art, informed by the present disclosure, that in order to restrain a detainee 90 from toppling or voluntarily tipping his torso onto floor 96, erection tether 100 will be installed in the following manner:

(1) Loop 102 will be passed through square ring 74, which is itself affixed to the rear portion of waist belt 42 (FIG. 6).

(2) Pileate fastening material segments 111, 112 will be temporarily joined by being pressed together, and thus loop 102 will be temporarily closed.

(3) Square ring 108 will be engaged with a hook 122 which is provided on wall 94 as part of the system of our present invention.

(4) Fasteners 111, 112 will be separated.

(5) Loop 102 will be drawn taut and then reclosed by pressing fasteners 111, 112 together.

(6) Pileate material patch 120 and headband 104 will be raised to the elevation of the brow of detainee 90 and then secured to loop 102 by pressing patch 120 against pileate material segment 111.

(7) Headband 104 will be closed around detainee's head and secured by pressing pileate material patch 116 against pileate material patch 118.

While the method of using erection tether 100 has been explained hereinabove in connection with a detainee seated in a police station booking room or the like, it is to be understood that erection tether 100 may also be used in other situations, e.g., during the transporting of the detainee in the rear seat of a police patrol vehicle; in which case hook 122 will be provided on the inside of the roof of the police patrol vehicle, projecting through the headliner.

When an erection tether of our invention is used in a police patrol vehicle, serious injury to the detainee due to vehicle accidents may be prevented, as well as preventing positional asphyxiation, damage to the patrol vehicle by the detainee, or self-inflicted injury produced by the detainee.

In accordance with another aspect of our invention, ring 108 of erection tether 100 may (in a police patrol vehicle) be alternatively attached to one end of an anchoring belt which extends over the seat back located behind the detainee, the opposite end of said anchoring belt being anchored to the floor of the vehicle trunk.

It will thus be seen that the objects set forth above, among those made apparent from the preceding description, are efficiently attained, and since certain changes may be made in the above constructions and the methods carried out thereby without departing from the scope of our present invention, it is intended that all matter contained in the above description or shown in the accompanying drawings shall be interpreted as illustrative only, and not in a limiting sense.

It is to be understood that many well known types of buckles, rings, fasteners, etc., may be substituted for the particular buckles, rings, etc., of the preferred embodiment of our invention shown and described herein without departing from the scope of our invention.

Further, the binder bodies of certain embodiments of our invention may be formed from foraminous sheet material such as high-strength netting or mesh, or perforated sheet material.

In certain embodiments of our invention the binder may be provided with but one leg flexure preventing member or steel.

Yet further, the leg flexure preventing means of certain embodiments of our invention may be angulated rather than rectilinear, whereby the detainee's legs may be held in flexed condition when bound in the binders of said certain embodiments.

Also, in certain embodiments of our invention the binding straps of the preferred embodiment may be replaced by other binder closure means such as pileate fastening means affixed to the overlapping edges of the binder body and confronting each other when the binder is wrapped about the legs of the detainee.

It is also to be understood that the following claims are intended to cover all of the generic and specific features of our invention hereindescribed, and all statements of the scope of our invention which, as a matter of language, might be said to fall therebetween.

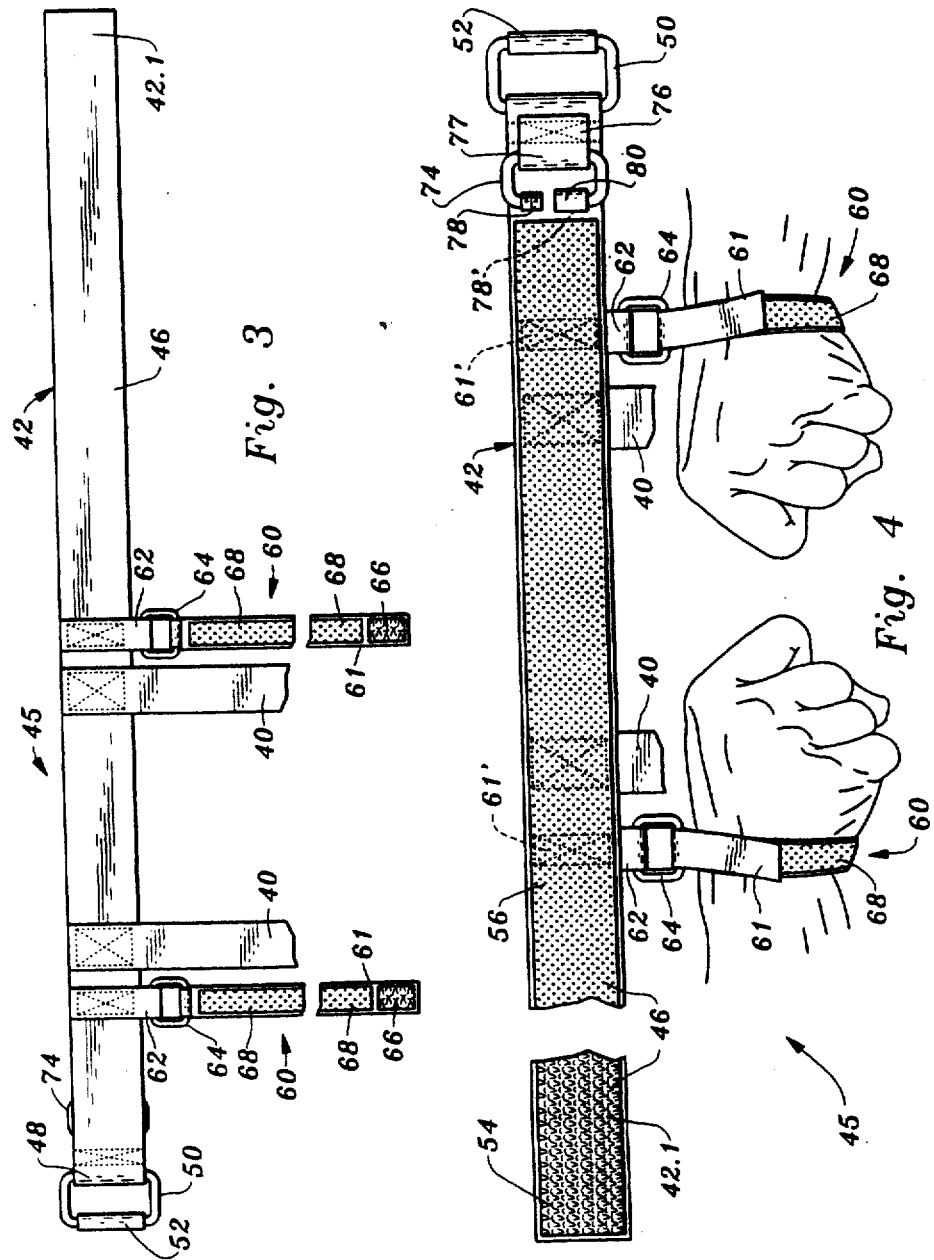

What we claim as new and desire to secure to ourselves by United States Letters Patent is:

1. A restraining device for restraining violent detainees, comprising:

leg binding means comprised of a body of high-strength, flexuous sheet material adapted to be wrapped around the legs of said detainee and having an upper edge and a lower edge opposed thereto, said upper edge being nearer to the buttocks of said detainee than to the knees of said detainee, and said lower edge being nearer to the ankles of said detainee then to the knees of said detainee wherein the length from the upper edge to the lower edge is equal to or less than the distance from a hip to an ankle of the detainee when said detainee is restrained in said restraining device;

closure means for maintaining said leg binding means closed about the legs of said detainee;

leg flexure preventing means attached to said leg binding means and adapted to extend from above to below the restrained knees of the detainee, comprising one or more supports substantially longitudinal with respect to straightened legs of the detainee, the leg flexure preventing means having a length equal to or less than the distance from a hip to an ankle of the detainee when said detainee is restrained in said restraining device and adapted to retain the legs of a detainee in a straight configuration; and retaining means comprising one or more flexible straps attached to the leg binding means and extending above the upper edge to attach to flexible means adapted to prevent doffing of the leg flexure preventing means and to permit raising the detainee to a sitting position.

2. A restraining device as claimed in claim 1, the flexible means to prevent doffing of the left flexure preventing means further comprising belt means adapted to be fastened about the body of the detainee.

3. A restraining device as claimed in claim 2, further comprising wrist positioning means attached to another part of said restraining device for immobilizing the wrists of said detainee.

4. A restraining device as claimed in claim 2, further comprising torso erecting means for maintaining the torso of said detainee in a substantially upright position, comprising an erection tether attached to the cincture means, said tether adapted to be secured to means for holding erect the detainee.

5. A restraining device as claimed in claim 4, further comprising head erecting means attached to the erection tether for maintaining the head of said detainee in a substantially upright position.

6. A restraining device as claimed in claim 2 in which each of said leg flexure preventing means is comprised of first and second rigid rectilinear portions and an intermediate portion which maintains an obtuse angle between said rectilinear portions.

7. A restraining device as claimed in claim 6 which is comprised of only one leg flexure preventing means.

8. A restraining device as claimed in claim 1 which is comprised of only one leg flexure preventing means.

9. A restraining device as claimed in claim 1 in which said sheet material of said leg binding means is foraminous.

10. A restraining device for restraining violet detainees, comprising;

leg binding means comprised of a body of high-strength, flexuous sheet material adapted to be wrapped around the legs of said detainee wherein the length from the upper edge to the lower edge is equal to or less than the distance from a hip to an ankle of the detainee when said detainee is restrained in said restraining device;

closure means for maintaining said leg binding means closed about the legs of said detainee;

leg flexure preventing means attached to said leg binding means and adapted to extend from above to below the restrained knees of the detainee, comprising one or more supports substantially longitudinal with respect to straightened legs of the detainee, the leg flexure preventing means having a length equal to or less than the distance from a hip to an ankle of the detainee when said detainee is restrained in said restraining device and adapted to retain the legs of a detainee in a straight configuration;

cincture means adapted to be fastened about the body of the detainee; and retaining means extending above the upper edge and attached to said leg binding means and to said cincture means for preventing the doffing of said leg binding means by said detainee.

11. A restraining device as claimed in claim 10, further comprising wrist positioning means attached to another part of said restraining device for immobilizing the wrists of said detainee.

12. A restraining device as claimed in claim 10, further comprising torso erecting means for maintaining the torso of said detainee in a substantially upright position.

13. A restraining device as claimed in claim 12, further comprising head erecting means for maintaining the head of said detainee in a substantially upright position.

14. A restraining device as claimed in claim 12 in which each of said leg flexure preventing means is comprised of first and second rigid rectilinear portions and an intermediate portion which maintains an obtuse angle between said rectilinear portions.

15. A restraining device as claimed in claim 10 which is comprised of only one leg flexure preventing means.

16. A restraining device as claimed in claim 10 in which said sheet material of said leg binding means is foraminous.

17. A restraining device as claimed in claim 10 which is comprised of only one leg flexure preventing means.

* * * * *

UNITED STATES PATENT AND TRADEMARK OFFICE
CERTIFICATE OF CORRECTION

PATENT NO. : 5,699,747
DATED : Dec. 23, 1997
INVENTOR(S) : Ronald J. O'Dell, et al It is certified that error appears in the above-identified patent and that said Letters Patent is hereby corrected as shown below:

The title page, should be deleted to be replaced with the attached title page.

The drawing sheets, consisting of Figs. 1 - 11, should be deleted to be replaced with the drawing sheets, consisting of Figs. 1 - 9, as shown on the attached pages.

Signed and Sealed this

Fourteenth Day of April, 1998

*Attest:*

BRUCE LEHMAN

*Attesting Officer*   Commissioner of Patents and Trademarks

United States Patent [19]

O'Dell et al.

[11] Patent Number: 5,699,747
[45] Date of Patent: Dec. 23, 1997

[54] APPARATUS FOR RESTRAINING VIOLENT DETAINEES

[76] Inventors: Ronald J. O'Dell, 6230 Lakeview Cir., San Ramon, Calif. 94583; Craig J. Zamolo, 1979 Mohawk Dr., Pleasant Hill, Calif. 94523

[21] Appl. No.: 595,598

[22] Filed: Feb. 2, 1996

[51] Int. Cl.⁶ .................................................. A61B 19/00
[52] U.S. Cl. ........................ 128/869; 128/870; 128/876
[58] Field of Search ........................... 128/845, 846, 128/869, 873, 874, 875, 876; 602/19; 5/648, 628, 631

[56] References Cited

U.S. PATENT DOCUMENTS

| | | |
|---|---|---|
| 1,043,648 | 11/1912 | Weaver . |
| 1,047,457 | 6/1912 | Steimer . |
| 2,361,328 | 10/1944 | Springer ................................ 5/628 |
| 2,489,828 | 11/1949 | Springer ................................ 5/625 |
| 2,899,692 | 8/1959 | Finken ................................... 5/628 |
| 3,399,670 | 9/1968 | Veasey . |
| 4,004,583 | 1/1977 | Johnson . |
| 4,027,869 | 6/1977 | Ruiz . |
| 4,173,974 | 11/1979 | Bellivean . |
| 4,204,534 | 5/1980 | Leary . |
| 4,706,957 | 11/1987 | Jackson . |
| 4,725,056 | 2/1988 | Rehd et al. . |
| 4,742,821 | 5/1988 | Wootan . |
| 4,841,961 | 6/1989 | Burdage et al. . |
| 4,860,560 | 8/1989 | Lindelius . |
| 4,910,818 | 3/1990 | Grahill et al. . |
| 5,016,650 | 5/1991 | Madar . |
| 5,027,456 | 7/1991 | Wadsworth . |
| 5,031,639 | 7/1991 | Wolfer . |
| 5,190,055 | 3/1993 | O'Connor . |
| 5,193,365 | 3/1993 | Nelson . |
| 5,243,724 | 9/1993 | Barnes . |
| 5,375,277 | 12/1994 | Carr ........................................ 5/628 |

*Primary Examiner*—Michael A. Brown

[57] ABSTRACT

Restraining methods and apparatus for restraining violent detainees, including a rigid binder for binding the upper and lower legs of the detainee, a waist belt, and suspender straps for joining the binder to the waist belt. An erection tether for maintaining the detainee erect by being tautly stretched between an attaching ring at the back of the waist belt and an overhead hook provided for the purpose of maintaining the detainee erect.

17 Claims, 11 Drawing Sheets

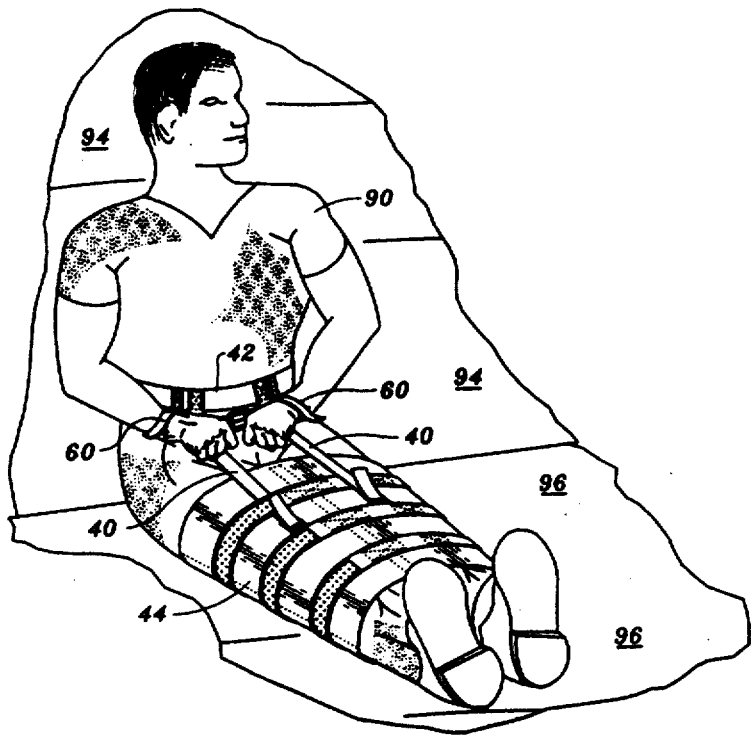

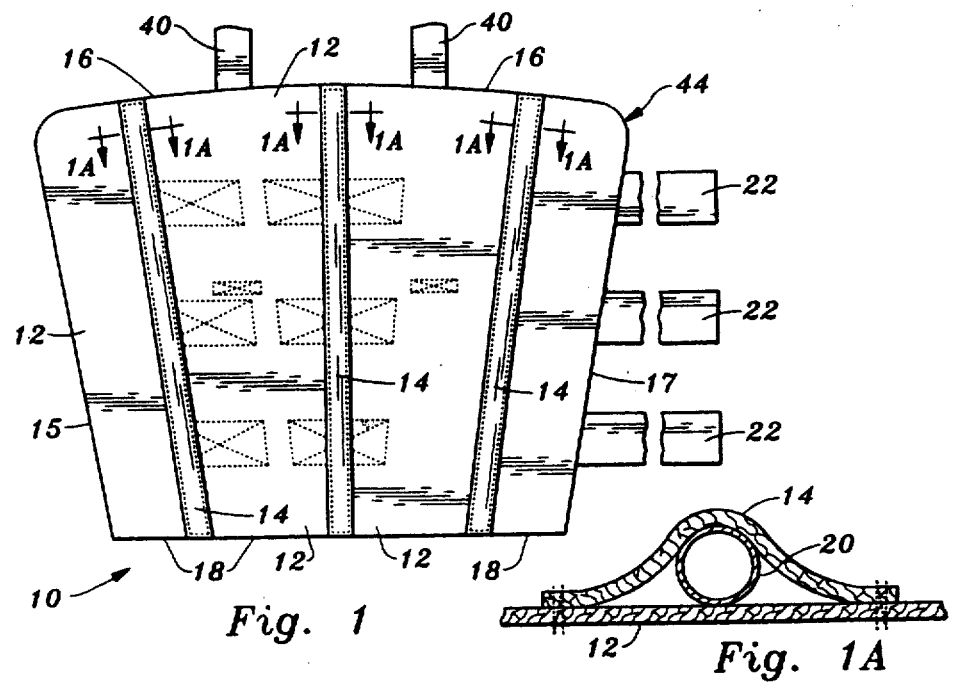
Fig. 1
Fig. 1A
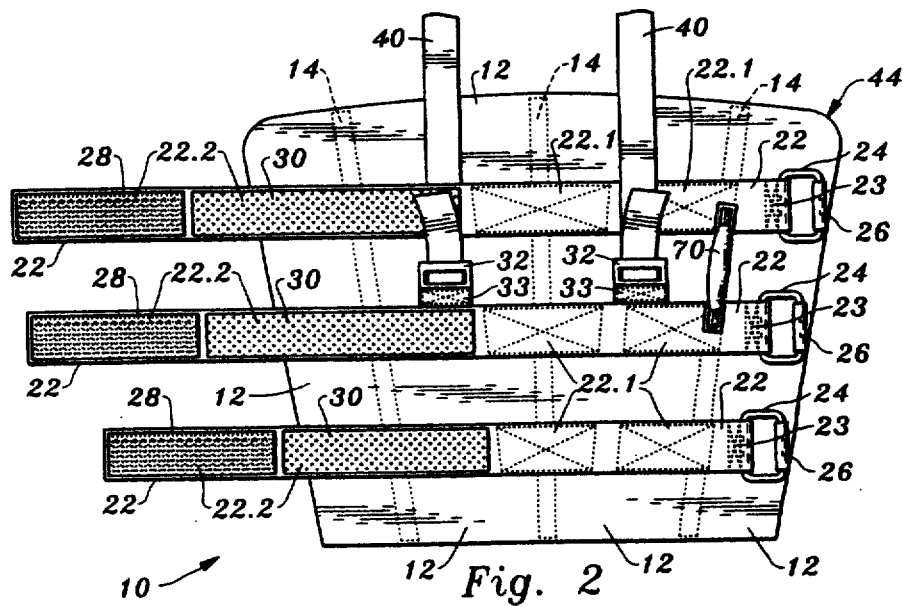
Fig. 2